United States Patent
Collins (10) Patent No.: US 9,192,422 B2
(45) Date of Patent: Nov. 24, 2015

(54) SYSTEM AND METHOD OF MATCHING IMPEDANCES OF AN ELECTROSURGICAL GENERATOR AND/OR A MICROWAVE GENERATOR

(75) Inventor: George J. Collins, Fort Collins, CO (US)

(73) Assignee: Covidien LP, Mansfield, MA (US)

( * ) Notice: Subject to any disclaimer, the term of this patent is extended or adjusted under 35 U.S.C. 154(b) by 1038 days.

(21) Appl. No.: 13/186,121

(22) Filed: Jul. 19, 2011

(65) Prior Publication Data

US 2013/0023867 A1 Jan. 24, 2013

(51) Int. Cl.
- A61B 18/12 (2006.01)
- A61B 18/00 (2006.01)
- A61B 18/18 (2006.01)

(52) U.S. Cl.
CPC ... *A61B 18/1206* (2013.01); *A61B 2018/00642* (2013.01); *A61B 2018/00648* (2013.01); *A61B 2018/00755* (2013.01); *A61B 2018/00779* (2013.01); *A61B 2018/00785* (2013.01); *A61B 2018/00827* (2013.01); *A61B 2018/00845* (2013.01); *A61B 2018/00875* (2013.01); *A61B 2018/00892* (2013.01); *A61B 2018/1823* (2013.01)

(58) Field of Classification Search
CPC .................. A61B 18/1206; A61B 2018/00642; A61B 2018/00648; A61B 2018/00755; A61B 2018/00779; A61B 2018/00785; A61B 2018/00827; A61B 2018/00845; A61B 2018/00875; A61B 2018/00892; A61B 2018/1823
USPC ................................................ 606/27, 34, 41
See application file for complete search history.

(56) References Cited

U.S. PATENT DOCUMENTS

| | | |
|---|---|---|
| D223,367 S | 4/1972 | Kountz |
| 4,204,549 A | 5/1980 | Paglione |
| D263,020 S | 2/1982 | Rau, III |
| D266,842 S | 11/1982 | Villers et al. |
| D278,306 S | 4/1985 | McIntosh |
| D295,893 S | 5/1988 | Sharkany et al. |
| D295,894 S | 5/1988 | Sharkany et al. |
| 5,300,068 A * | 4/1994 | Rosar et al. ..................... 606/34 |
| 5,323,778 A | 6/1994 | Kandarpa et al. |
| 5,364,392 A | 11/1994 | Warner et al. |
| D354,218 S | 1/1995 | Van de Peer |
| 5,406,503 A * | 4/1995 | Williams et al. .............. 702/106 |
| 5,672,173 A * | 9/1997 | Gough et al. ................... 606/41 |

(Continued)

FOREIGN PATENT DOCUMENTS

| | | |
|---|---|---|
| CN | 1103807 | 6/1995 |
| DE | 390937 | 3/1924 |

(Continued)

OTHER PUBLICATIONS

U.S. Appl. No. 08/136,098, filed Oct. 14, 1993, Roger A. Stern.

(Continued)

*Primary Examiner* — Michael Peffley
*Assistant Examiner* — Daniel Fowler (57) ABSTRACT

A system for performing a surgical procedure includes a source of energy, a surgical instrument, and an impedance matching network. The source of energy is an electrosurgical generator or a microwave generator. The surgical instrument is coupled to the source of energy and receives the energy therefrom. The surgical instrument is adapted to treat tissue with the energy. The impedance matching network is interposed along a path of the energy and matches an input impedance of the source of energy to an output impedance (or thereabouts).

19 Claims, 5 Drawing Sheets

(56) References Cited

U.S. PATENT DOCUMENTS

| | | | |
|---|---|---|---|
| 5,817,093 A * | 10/1998 | Williamson et al. | 606/50 |
| 5,957,969 A | 9/1999 | Warner et al. | |
| 5,961,871 A | 10/1999 | Bible et al. | |
| D424,693 S | 5/2000 | Pruter | |
| D424,694 S | 5/2000 | Tetzlaff et al. | |
| D425,201 S | 5/2000 | Tetzlaff et al. | |
| 6,216,704 B1 | 4/2001 | Ingle et al. | |
| D449,886 S | 10/2001 | Tetzlaff et al. | |
| D457,958 S | 5/2002 | Dycus et al. | |
| D457,959 S | 5/2002 | Tetzlaff et al. | |
| 6,428,537 B1 | 8/2002 | Swanson et al. | |
| 6,629,974 B2 | 10/2003 | Penny et al. | |
| D487,039 S | 2/2004 | Webster et al. | |
| 6,723,091 B2 | 4/2004 | Goble et al. | |
| 6,784,405 B2 | 8/2004 | Flugstad et al. | |
| D496,997 S | 10/2004 | Dycus et al. | |
| D499,181 S | 11/2004 | Dycus et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| 7,200,010 B2 | 4/2007 | Broman et al. | |
| D541,938 S | 5/2007 | Kerr et al. | |
| 7,305,311 B2 | 12/2007 | van Zyl | |
| D564,662 S | 3/2008 | Moses et al. | |
| D576,932 S | 9/2008 | Strehler | |
| 7,513,896 B2 | 4/2009 | Orszulak | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| D634,010 S | 3/2011 | DeCarlo | |
| 7,927,328 B2 | 4/2011 | Orszulak et al. | |
| 2004/0106917 A1* | 6/2004 | Ormsby et al. | 606/33 |
| 2007/0129716 A1* | 6/2007 | Daw et al. | 606/34 |
| 2008/0015570 A1 | 1/2008 | Ormsby et al. | |
| 2009/0018536 A1 | 1/2009 | Behnke | |
| 2009/0076492 A1* | 3/2009 | Behnke | 606/33 |
| 2009/0157073 A1 | 6/2009 | Orszulak | |
| 2009/0237169 A1 | 9/2009 | Orszulak | |
| 2009/0299360 A1 | 12/2009 | Ormsby | |
| 2010/0030107 A1* | 2/2010 | Hancock | 600/567 |
| 2010/0076424 A1 | 3/2010 | Carr | |
| 2010/0079215 A1 | 4/2010 | Brannan et al. | |
| 2010/0082022 A1 | 4/2010 | Haley et al. | |
| 2010/0082023 A1 | 4/2010 | Brannan et al. | |
| 2010/0082024 A1 | 4/2010 | Brannan et al. | |
| 2010/0082025 A1 | 4/2010 | Brannan et al. | |
| 2010/0082083 A1 | 4/2010 | Brannan et al. | |
| 2010/0082084 A1 | 4/2010 | Brannan et al. | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| GB | 2 434 872 | 8/2007 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001003776 | 1/2001 |
| JP | 2001008944 | 1/2001 |
| JP | 2001029356 | 2/2001 |
| JP | 2001037775 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO 00/48672 | 8/2000 |
| WO | WO 2004/047659 | 6/2004 |
| WO | WO 2005/115235 | 12/2005 |
| WO | WO 2007/055491 | 5/2007 |
| WO | WO 2008/043999 | 4/2008 |
| WO | WO 2008/044000 | 4/2008 |
| WO | WO 2008/044013 | 4/2008 |
| WO | WO 2008/071914 | 6/2008 |
| WO | WO2008/110756 | 9/2008 |
| WO | WO2010/035831 | 4/2010 |

OTHER PUBLICATIONS

U.S. Appl. No. 08/483,742, filed Jun. 7, 1995, Roger A. Stern.
U.S. Appl. No. 12/861,333, filed Aug. 23, 2010, Joseph D. Brannan.
U.S. Appl. No. 12/944,951, filed Nov. 12, 2010, Joseph D. Brannan.

(56) References Cited

OTHER PUBLICATIONS

U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/113,736, filed May 23, 2011, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/267,369, filed Oct. 6, 2011, Prakash et al.
U.S. Appl. No. 13/268,143, filed Oct. 7, 2011, Kenlyn S. Bonn.
U.S. Appl. No. 13/281,605, filed Oct. 26, 2011, Prakash et al.
U.S. Appl. No. 13/290,462, filed Nov. 7, 2011, Kenlyn S. Bonn.
U.S. Appl. No. 13/298,461, filed Nov. 17, 2011, Buysse et al.
U.S. Appl. No. 13/344,753, filed Jan. 6, 2012, Lee et al.
U.S. Appl. No. 13/343,788, filed Jan. 5, 2012, William O. Reid Jr.
U.S. Appl. No. 13/343,798, filed Jan. 5, 2012, William O. Reid Jr.
U.S. Appl. No. 13/344,790, filed Jan. 6, 2012, Lee et al.
U.S. Appl. No. 13/351,463, filed Jan. 17, 2012, Smith et al.
U.S. Appl. No. 13/351,553, filed Jan. 17, 2012, Mahajan et al.
U.S. Appl. No. 13/358,129, filed Jan. 25, 2012, Joseph D. Brannan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization." Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•Llnear Thermal Transport in Biological Media", Proc. ASME HTD-355, 131 (1997).

(56) References Cited

OTHER PUBLICATIONS

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, " LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.-Medical Professionals: Targis™ Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.

(56) References Cited

OTHER PUBLICATIONS

Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.

(56) References Cited

OTHER PUBLICATIONS

European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11004942 dated Sep. 23, 2011.
European Search Report EP 11174318.3 dated Nov. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.

\* cited by examiner

SYSTEM AND METHOD OF MATCHING IMPEDANCES OF AN ELECTROSURGICAL GENERATOR AND/OR A MICROWAVE GENERATOR

BACKGROUND

1. Technical Field

The present disclosure relates to using electromagnetic energy to treat tissue. More particularly, the present disclosure relates to a system and method of matching impedances of an electrosurgical generator and/or a microwave generator.

2. Description of Related Art

Historically, surgery was performed using only mechanical tools, such as mechanical cutting instruments, scalpels, bladed forceps, saws and the like. However, in recent years, technology has improved such that surgeons now frequently use electromagnetic waves to cause a wider variety of surgical effects, e.g., by selectively modifying tissue using electromagnetic energy to produce a specific effect. The characteristics of the electromagnetic energy applied to tissue strongly correlates to the effect that the energy has on the tissue. These characteristics are therefore changed in accordance with the desired tissue effect. Two types of electromagnetic energy that are commonly applied during surgery include electrosurgical energy and microwave energy.

Electrosurgery is surgery using electrosurgical energy. Electrosurgery involves the application of electrosurgical energy (e.g., "RF energy") to cut, dissect, ablate, coagulate, seal tissue, or otherwise treat biological tissue during a surgical procedure. Additionally, certain electrosurgical modes invoke the application of electric spark to biological tissue, for example, human flesh or the tissue of internal organs, without significant cutting. The spark is produced by bursts of radio-frequency electrical energy generated from an appropriate electrosurgical generator. Generally, fulguration is used to coagulate, cut or blend body tissue. Coagulation is defined as a process of desiccating tissue wherein the tissue cells are ruptured and dehydrated/dried. Electrosurgical cutting, on the other hand, includes applying an electrical spark to tissue in order to produce a cutting or dividing effect. Blending includes the function of cutting combined with the production of a hemostasis effect.

Generally, electrosurgery utilizes an electrosurgical generator, an active electrode and a return electrode. The electrosurgical generator generates electrosurgical energy typically above 100 kilohertz to avoid muscle and/or nerve stimulation between the active and return electrodes when applied to tissue. During electrosurgery, current generated by the electrosurgical generator is conducted through the patient's tissue disposed between the two electrodes. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The current causes the tissue to heat up as the electromagnetic wave overcomes the tissue's impedance. Although many other variables affect the total heating of the tissue, usually more current density directly correlates to increased heating.

Microwave surgical procedures invoke the application of microwave energy to tissue. Unlike low frequency RF therapy that heats tissue with current, microwave therapy heats tissue within the electromagnetic field delivered by an energy delivery device (e.g., a microwave antenna). Microwave surgical procedures typically utilize a microwave generator and an energy delivery device that delivers the microwave energy to the target tissue. One type of energy delivery device is a coaxial microwave antenna that forms an approximate dipole antenna. Microwave surgical systems involve applying microwave radiation to heat, ablate and/or coagulate tissue. For example, treatment of certain diseases requires destruction of malignant tissue growths (e.g., tumors) or surrounding tissue. It is known that tumor cells denature at elevated temperatures that are slightly lower than temperatures injurious to surrounding healthy cells. Therefore, by applying microwave energy to heat tumor cells to temperatures above 41° C. kills the tumor cells while adjacent healthy cells are maintained at lower temperatures avoiding irreversible cell damage. Another method used to treat diseased tissue is to resect a portion of the diseased organ, tissue or anatomical structure. For example, a liver may contain diseased tissue and healthy tissue. One treatment option is to pre-coagulate and ablate some of the liver tissue to facilitate resection of a portion of the liver including the diseased tissue. Microwave energy can be used during these types of procedures to pre-coagulate tissue prior to resection, to reduce bleeding during resection and to facilitate the actual resection of the tissue.

The microwave energy may be applied via an antenna that can penetrate tissue. There are several types of microwave antennas, such as monopole and dipole antennas. In monopole and dipole antennas, most of the microwave energy radiates perpendicularly away from the axis of the conductor. A monopole antenna includes a single, elongated conductor that transmits the microwave energy. A typical dipole antenna has two elongated conductors parallel to each other and positioned end-to-end relative to one another with an insulator placed therebetween. Each of the conductors is typically about ¼ of the length of the wavelength of the microwave energy making the aggregate length of both conductors about ½ of the wavelength of the microwave energy.

Both sources of energy used during modern surgical procedures share some common characteristics. Microwave and electrosurgical generators both apply electromagnetic energy and include input impedances. Also, each utilizes a surgical instrument that directs the energy to the target tissue. Additionally, while the energy is applied to the tissue, the tissue is affected and its characteristics change as a result of the application of the energy. For example, microwave energy can cause tissue to heat up causing water to boil therein. This reduction in hydration causes the tissue's impedance to increase. Likewise, an electrosurgical instrument can also cause tissue to produce an analogous increase in impedance from dehydration when applying electrosurgical energy thereto.

SUMMARY

The present disclosure relates to using electromagnetic energy to treat tissue. More particularly, the present disclosure relates to a system and method of matching impedances of an electrosurgical generator and/or a microwave generator.

In one embodiment of the present disclosure, a system for performing a surgical procedure includes a source of energy, a surgical instrument and an impedance matching network. The source of energy is either an electrosurgical generator or a microwave generator. The surgical instrument couples to the source of energy and receives energy therefrom. The surgical instrument treats tissue with the energy. The impedance matching network is interposed along a path of the energy and matches an input impedance of the source of the energy to an output impedance (or thereabouts). The source of the energy may include the impedance matching network.

In one embodiment of the present disclosure, the impedance matching network continuously matches the input impedance of the source of the energy to about the output impedance. Additionally or alternatively, the impedance measurement component intermittently estimates the output impedance and operatively communicates the estimated output impedance to the impedance matching network. The impedance matching network can intermittently match the input impedance of the source of the energy to about the output impedance in accordance with the communicated and estimated output impedance.

In another embodiment of the present disclosure, the system includes a control component, a measurement component, power measurement component and an impedance measurement component. The power measurement component measures energy and estimates one or more of a total power delivered to tissue, a power reflectance, an instantaneous power delivery to tissue, an energy transfer efficiency, and an S-parameter.

The measurement component estimates one or more of a voltage, a current, a duty cycle, a frequency, a power level, an energy efficiency, a reflectance, a wattage, a total power delivered, a power factor, an instantaneous power delivery and a S-parameter. The impedance measurement component estimates the input impedance of the source of the energy and/or the output impedance.

The control component is coupled to the impedance matching network. The control component controls one or more parameter of the impedance matching network to match the input impedance of the source to about the output impedance. The parameters may be one or more of a capacitance, an impedance, an inductance and a resistance. The impedance matching network may utilize one or more matching elements, e.g., one of a balun, a π-network, a T-network, a capacitor, a resistor, a variac, a transformer, an inductor, a variable capacitor, a vacuum variable capacitor, a PIN diode, an RF PIN diode, a FET, a MEMS device, a chip cap, a solid state switch network of chip caps, a stub tuned PC board reactance and a motor driven variable reactive element. Additionally or alternatively, the impedance matching network has a capacitance formed from a network having a PIN diode array.

In another embodiment of the present disclosure, a generator for surgical treatment of tissue includes an energy output stage, a surgical instrument interface and an impedance matching network. The energy output stage may be either a RF output stage configured to generate electrosurgical energy or a microwave output stage configured to generate microwave energy. The energy output stage generates energy and is one of electrosurgical energy and microwave energy. The surgical instrument interface is coupled to a surgical instrument configured to treat tissue with the energy. The source of the energy communicates the energy to the surgical instrument interface. The impedance matching network is interposed along a path of the energy between the source of the energy and the surgical instrument interface. The impedance matching network matches an input impedance of the generator to an output impedance (or thereabouts).

In yet another embodiment of the present disclosure, a method of performing a surgical procedure includes: providing a source of energy (e.g., the energy is one of electrosurgical energy and microwave energy); positioning a surgical instrument configured to receive the energy (e.g., the surgical instrument is positioned into and/or adjacent to a portion of target tissue to direct the energy to treat the target tissue); and matching an input impedance of the source of the energy to about an output impedance. The method may also include one or more of: activating the source of the energy; estimating the output impedance; and/or adjusting an effective capacitance between the input and output impedances thereby matching the input impedance to about the output impedance.

BRIEF DESCRIPTION OF THE DRAWINGS

These and other advantages will become more apparent from the following detailed description of the various embodiments of the present disclosure with reference to the drawings wherein.

DETAILED DESCRIPTION

Particular exemplary embodiments of the present disclosure are described hereinbelow with reference to the accompanying drawings. In the following description, well-known functions or constructions are not described in detail to avoid obscuring the present disclosure in unnecessary detail.

Figure 1:
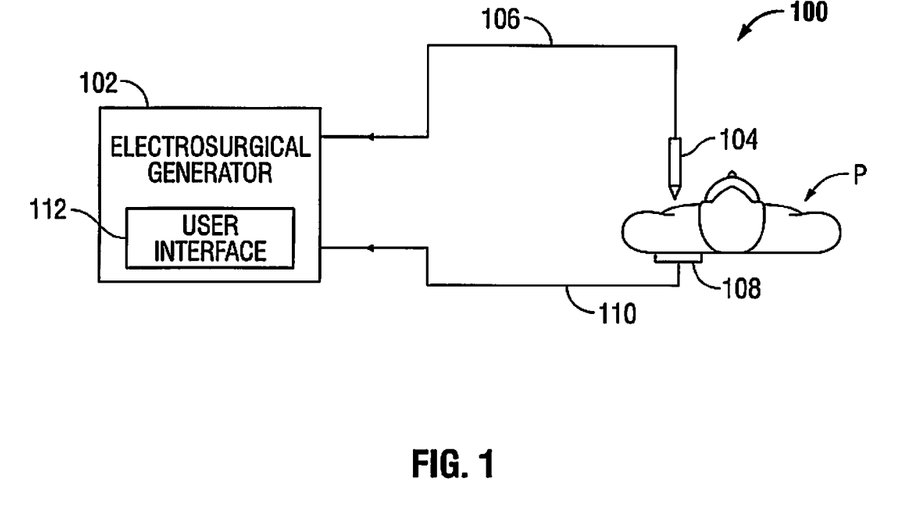
FIG. 1 is a block diagram of an electrosurgical system in accordance with the present discourse.

Referring to the drawings, FIG. 1 is a block diagram of an electrosurgical system 100 in accordance to an embodiment of the present discourse. Electrosurgical system 100 includes an electrosurgical generator 102 operatively coupled to a surgical instrument 104 that directs electrosurgical energy to target tissue of patient P. Although electrosurgical instrument 104 is shown in the monopolar configuration, it is the purview of one of ordinary skill in the art to use a bipolar electrosurgical instrument (e.g., sealing forceps) with system 100. Electrosurgical instrument 104 is coupled to electrosurgical generator 102 via cable 106. Electrosurgical generator 102 supplies the electrosurgical energy to cable 106 which guides the electrosurgical energy to electrosurgical instrument 104. The electrosurgical energy flows through patient P and returns from patient P to system 100 via return pad 108. Return pad 108 is coupled to cable 110 which guides the returning electrosurgical energy to electrosurgical generator 102. Electrosurgical generator 102 also includes user interface 112.

Figure 2:
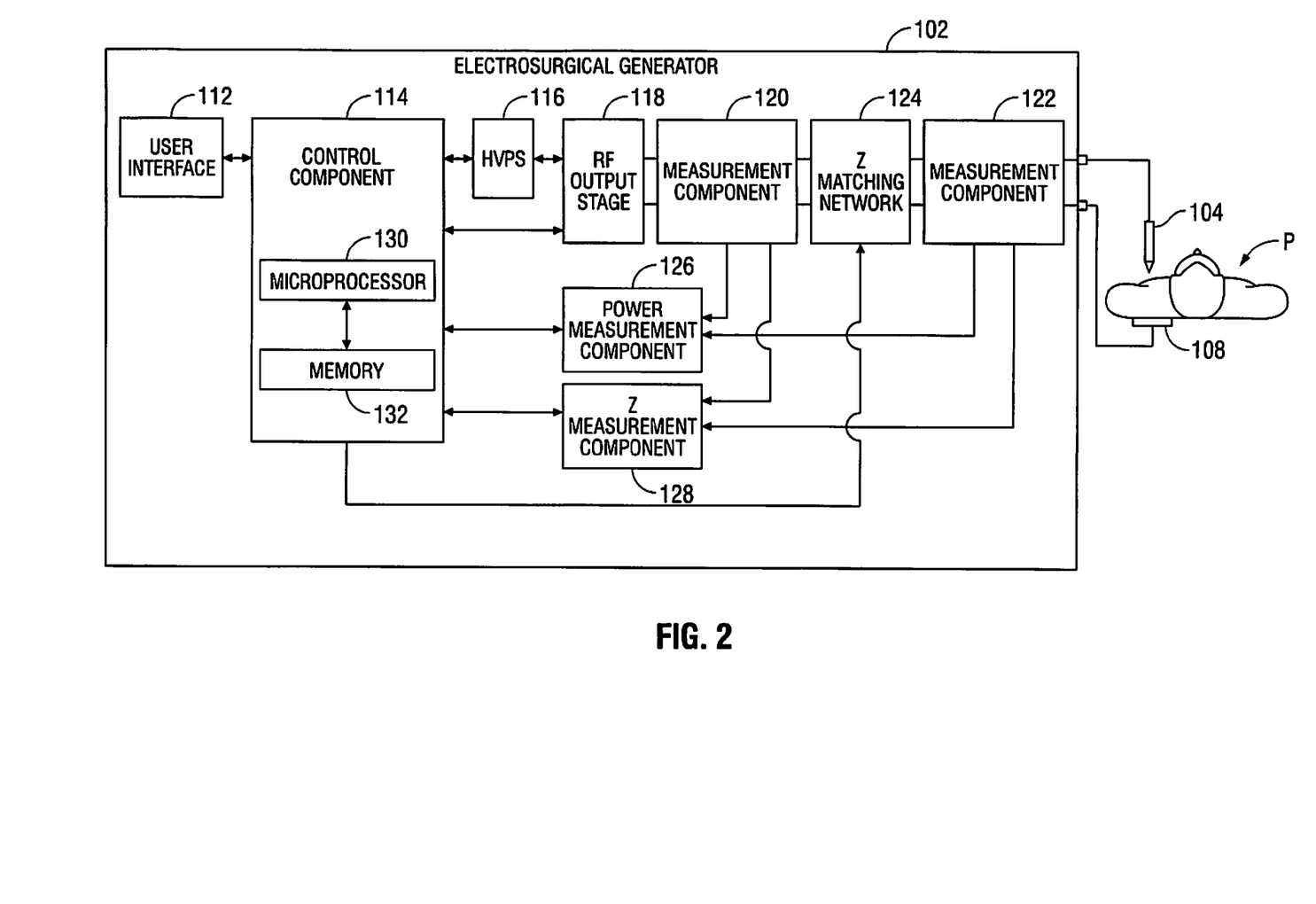
FIG. 2 is a block diagram of the electrosurgical generator shown in FIG. 1 in accordance with the present disclosure.

Referring to the drawings, FIG. 2 is a block diagram of the electrosurgical generator 102 shown in FIG. 1 in accordance with the present disclosure. Electrosurgical generator 102 includes a user interface 112, a control component 114, a high voltage DC power supply 116 ("HVPS"), an RF output stage 118, measurement components 120 and 122, an impedance matching network 124, a power measurement component 126, and an impedance measurement component 128. Electrosurgical generator 102 may be implemented in (or some combination thereof) hardware, software, software in execution, firmware, microcode, bytecode, in virtualization, in a hardware description language, using logic gates, circuitry, digital circuitry, CPLDs, FPGAs, RAM, ROM, MEMS and the like. User interface 112 receives user input and provides the user input to control component 114 for control of electrosurgical generator 102. Control component 114 interprets the user input and controls operation of electrosurgical generation 102 in accordance therewith.

Electrosurgical instrument 104 has one or more active electrodes for treating tissue of patient P. Electrosurgical instrument 104 maybe any type of electrosurgical instrument (e.g., monopolar or bipolar) and may include active electrodes designed for a wide variety of electrosurgical procedures (e.g., electrosurgical cutting, ablation, etc.). Electrosurgical energy is supplied to electrosurgical instrument 104 by electrosurgical generator 102 via cable 106, which is connected to an active output terminal, allowing electrosurgical instrument 104 to coagulate, ablate, and/or otherwise treat tissue by causing hemostasis. The electrosurgical energy is returned to electrosurgical generator 102 through return pad 108 via cable 110 after passing through patient P.

The electrosurgical generator 102 includes user interface 112 (e.g., buttons, activators, switches, touch screen, etc.) for controlling electrosurgical system 100. In addition, electrosurgical generator 102 includes one or more display screens (not explicitly shown) for providing the user with variety of output information (e.g., intensity settings, treatment complete indicators, etc.). The user interface 112 allows the user (e.g., a surgeon, nurse, or technician) to adjust the electrosurgical energy parameters (e.g., power, waveform, duty cycle, voltage, current, frequency, and/or other parameters) to achieve the desired electrosurgical energy characteristics suitable for a particular task (e.g., coagulating, tissue sealing, intensity setting, etc.). Additionally or alternatively, user interface 112 may include a settable desired tissue effect (e.g., hemostasis, coagulation, ablation, dissection, cutting, and/or to sealing tissue). The electrosurgical instrument 104 may also include one or more input controls (not explicitly shown) that may be redundant with user interface 112 of electrosurgical generator 102. Placing the input controls on the electrosurgical instrument 104 allows for easier and faster modification of the electrosurgical energy during the surgical procedure without requiring interaction with electrosurgical generator 102.

Control component controls HVPS 116, RF output stage 118 and impedance matching network 124 (discussed in more detail below). HVPS 206 provides high voltage DC power to RF output stage 208, which then converts high voltage DC power into electrosurgical energy and delivers the electrosurgical energy to electrosurgical instrument 104. In particular, RF output stage 208 generates sinusoidal waveforms of electrosurgical energy. RF output stage 208 generates a plurality of waveforms having various duty cycles, peak voltages, crest factors and other suitable parameters. Certain types of waveforms are suitable for specific electrosurgical modes. For instance, RF output stage 208 generates a 100% duty cycle sinusoidal waveform in cut mode, which is best suited for ablating, fusing and dissecting tissue, and a 1-25% duty cycle waveform in coagulation mode, which is best used for cauterizing tissue to stop bleeding.

Control component 114 includes a microprocessor 130 operably connected to a memory 132, which may be volatile type memory (e.g., RAM) and/or non-volatile type memory (e.g., flash media, disk media, etc.). Control component 114 includes an output port that is operably connected to the HVPS 116 and/or RF output stage 118 that allows the control component 114 to control the output of electrosurgical generator 102 according to either open and/or closed control loop schemes. Control component 114 may include any suitable circuitry, e.g., a logic processor (e.g., control circuit), hardware, software, firmware, or any other logic control adapted to perform the features discussed herein.

Electrosurgical generator 102 includes measurement components 120 and 122 for measuring a variety of tissue and energy properties (e.g., voltage, a current, a duty cycle, a frequency, a power level, an energy efficiency, a reflectance, a wattage, a total power delivered, a power factor, an instantaneous power delivery and a S-parameter etc.) and to provide feedback to the control component 114 based on the measured properties. Power measurement component 126 utilizes the sensed properties from measurement components 120 and/122 to estimate one or more of a total power delivered to tissue, a power reflectance, an instantaneous power delivery to tissue, an energy transfer efficiency, a S-parameter and the like. Additionally or alternatively, impedance measurement component also can utilize measurement component 120 and/or 122 to estimate the input impedance and/or the output impedance. Such sensors are within the purview of those skilled in the art. Control component 114 sends signals to HVPS 206 and/or RF output stage 208 to control the DC and/or RF power supplies, respectively. Control component 114 also receives input signals from the user interface 112 of the electrosurgical generator 102 or from electrosurgical instrument 104. Control component 114 utilizes the input signals to adjust the output power or the electrosurgical waveform of the electrosurgical generator 102 and/or perform other control functions therein. For example, control component 114 may utilize a feedback loop control algorithm such as a proportional-integral-derivative (P-I-D) control algorithm.

Control component 114 utilizes the information received from power measurement component 126, impedance measurement component 128, and/or measurement components 120 and 122 to control impedance matching network 124. Impedance matching network 124 matches the input impedance of electrosurgical generator 102 to the output impedance. The impedance matching network 124 may implement several types of impedance matching including: (1) matching the input impedance to the output impedance to maximize the power transfer, (2) matching the input impedance to the output impedance to minimize reflections, (3) matching the real impedance of the input impedance to the real impedance of the output impedance, and/or (4) matching the input impedance to the output impedance such that the output impedance is the complex conjugate of the input impedance. These types of impedance matching are not necessarily exclusive to each other. For example, types (1) and (2) may be performed simultaneously.

The matching network 124 may include one or more matching elements, including: a balun, a π-network, a T-network, a capacitor, a resistor, a variac, a transformer, an inductor, a variable capacitor, a vacuum variable capacitor, a PIN diode, an RF PIN diode, a FET, a MEMS device, a chip cap, a solid state switch network of chip caps, a stub tuned PC board reactance and a motor driven variable reactive element.

Control component 114 can communicate to impedance matching network 124 using data control or direct control. The communications may be continuous or intermittent. The data may be communicated in analog form, digital form, using a pulse width modulated signal, using a frequency or analog modulated signal, or any other communication technology. Control component 114 may use the data to form a feedback control loop such as a P-I-D control algorithm. Additionally or alternatively, control component 114 may control the generation of the electrosurgical energy by applying a feed-forward control technique.

Figure 3:
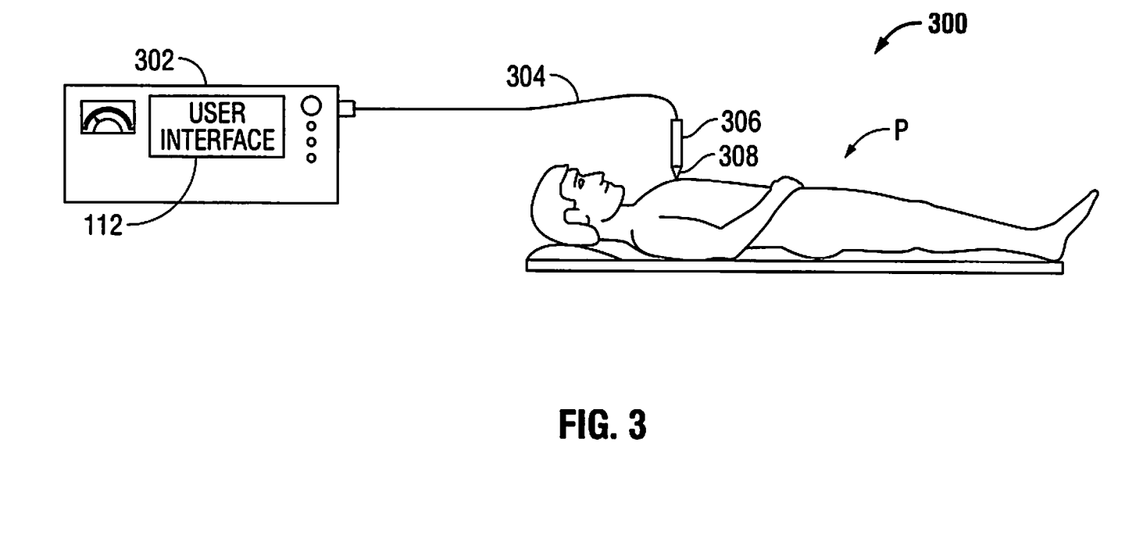
FIG. 3 is a block diagram of a microwave surgical system in accordance with the present disclosure.

Referring to the drawings, FIG. 3 is a block diagram of a microwave surgical system 300 in accordance with the present disclosure. Microwave surgical system 300 includes microwave generator 302 which is controlled by user interface 112. Microwave generator 302 generates microwave energy for application to tissue of patient P. Microwave energy travels along a cable 304 to a surgical instrument 306. Surgical instrument 306 includes an antenna 308 which applies the microwave energy to tissue of patient P. Surgical instrument 306 can ablate tissue, may be used for resection of tissue, and the like.

User interface 112 may select among several modes and/or settings. User interface 112 may include several types of input (e.g., buttons, activators, switches, touch screen, etc.) for microwave surgical system 300. In addition, microwave surgical system 300 includes one or more display screens (not explicitly shown) for providing the user with variety of output information (e.g., intensity settings, treatment complete indicators, etc.). The user interface 112 allows the user (e.g., a surgeon, nurse, or technician) to adjust the microwave energy parameters (e.g., power, waveform, duty cycle, voltage, current, frequency, and/or other parameters) to achieve the desired characteristics suitable for a particular task or particular type of tissue (e.g., resection of various tissue types or organs). The surgical instrument 306 may also include one or more input controls (not explicitly shown) that may be redundant with user interface 112 of microwave generator 302.

Figure 4:
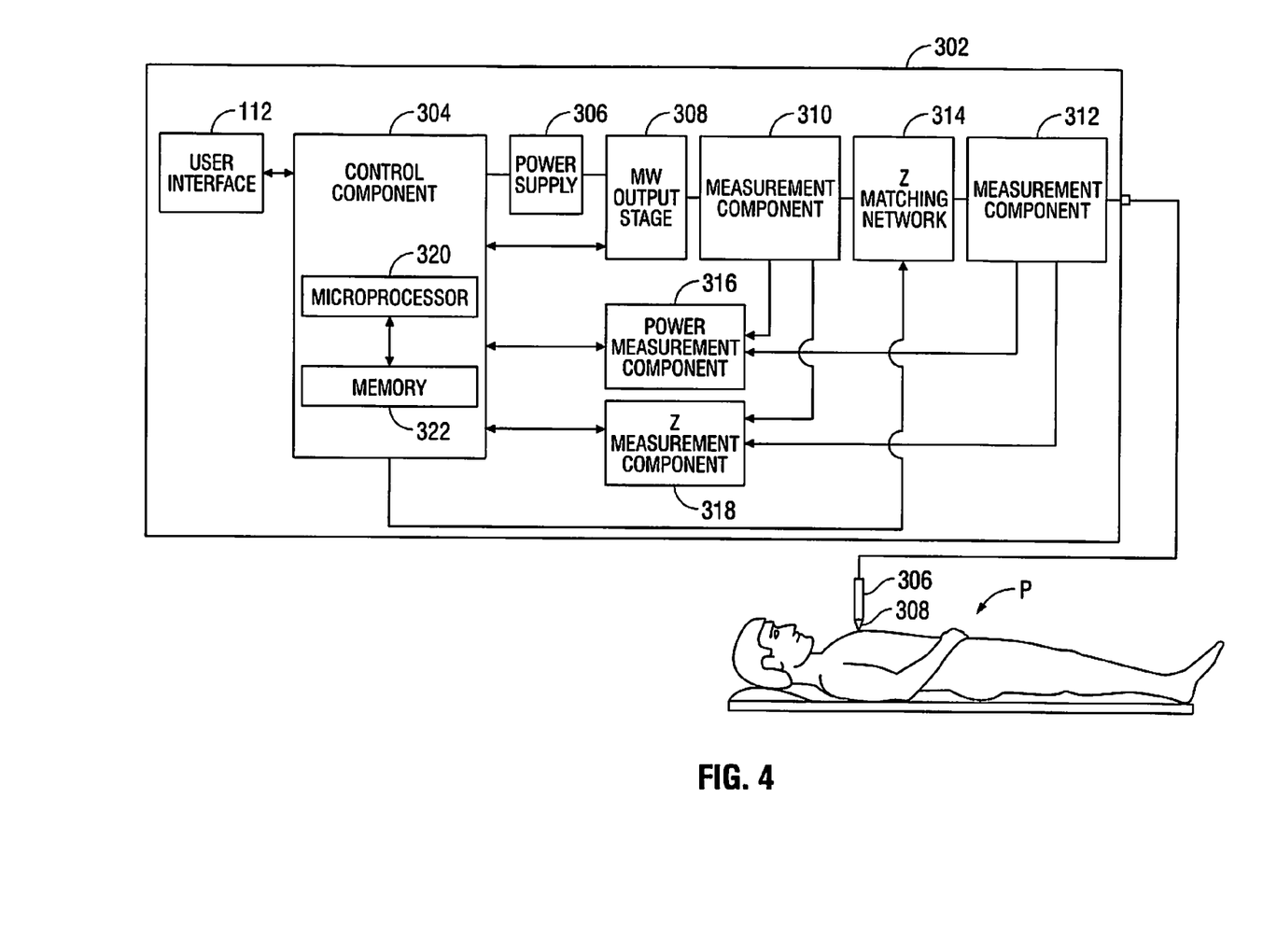
FIG. 4 is a block diagram of the microwave generator shown in FIG. 3 in accordance with the present disclosure.

Referring to the drawings, FIG. 4 is a block diagram of the microwave generator 302 shown in FIG. 3 in accordance with the present disclosure. Microwave generator 302 includes user interface 112, a control component 304, a power supply 306, a microwave output stage 308, measurement components 310 and 312, impedance matching network 314, a power measurement component 316, and an impedance measurement component 318. Control component 304 controls the operation of microwave generator 302 and includes a microprocessor 320 and a memory 322. Control component 304 controls power supply 306 which supplies DC power to microwave output stage 308. Microwave output stage 308 generates microwave energy to supply surgical instrument 306 with microwave energy for application to patient P via antenna 308.

The microwave energy from microwave output stage 308 is estimated by measurement component 310 and 312. Measurement components 310 and 312 estimate voltage, current, duty cycle, frequency, power level, energy efficiency, reflectance, wattage, total power delivered, power factor, instantaneous power delivery, and S-parameters of the microwave energy. These estimated values are utilized by power measurement component 316 and impedance measurement component 318. Power measurement component 316 estimates total power delivered to tissue, power reflectance, instantaneous power delivery to tissue, energy transfer efficiency, and S-parameters. Impedance measurement component 318 can estimate the input impedance or output impedance using measurement components 310 and 312, and communicates the estimated impedances to control component 304. Control component controls impedance matching network 314. Impedance matching network 314 matches the input impedance to the output impedance. The impedance matching network 314 can intermittently or continuously match the input impedance to the output impedance.

The impedance matching network 314 may include one or more of the following matching elements: a balun, a π-network, a T-network, a capacitor, a resistor, a variac, a transformer, an inductor, a variable capacitor, a vacuum variable capacitor, a PIN diode, an RF PIN diode, a FET, a MEMS device, a chip cap, a solid state switch network of chip caps, a stub tuned PC board reactance and a motor driven variable reactive element. As previously mentioned, impedance matching may be one or more of several types including: (1) matching the input impedance to the output impedance to maximize the power transfer, (2) matching the input impedance to the output impedance to minimize reflections, (3) matching the real impedance of the input impedance to the real impedance of the output impedance, and/or (4) matching the input impedance to the output impedance such that the output impedance is the complex conjugate of the input impedance.

Figure 5:
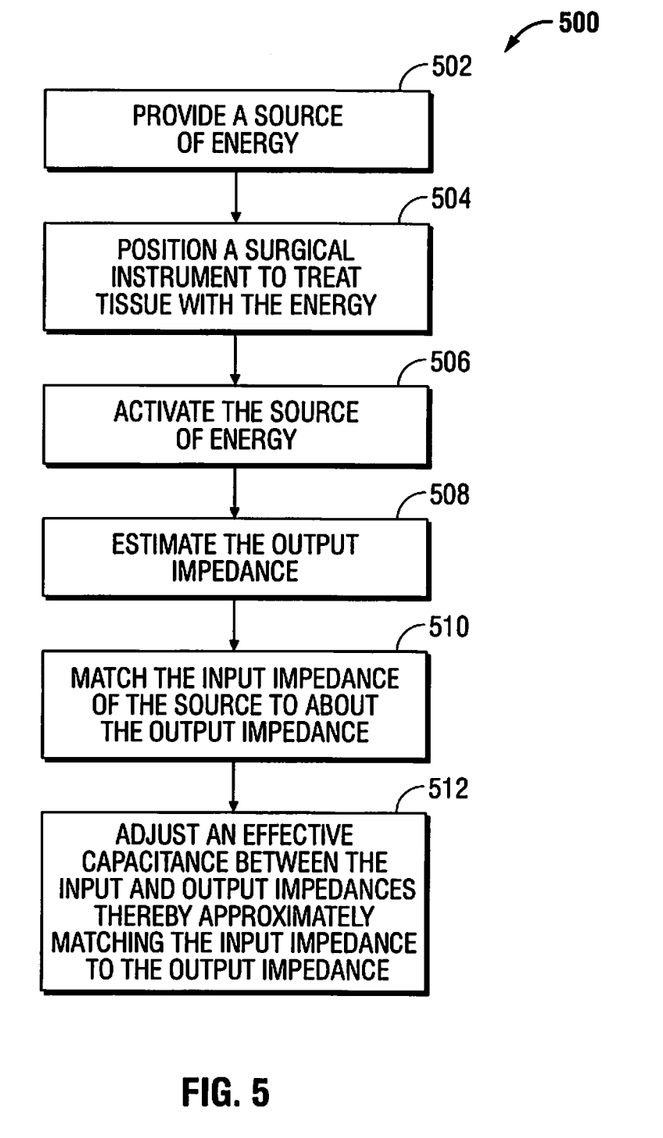
FIG. 5 is a flow chart diagram of a method of performing a surgical procedure utilizing microwave energy or electrosurgical energy in accordance with the present disclosure.

Referring to the drawings, FIG. 5 shows a flow chart diagram of a method 500 of performing a surgical procedure utilizing microwave energy or electrosurgical energy in accordance with the present disclosure. Method 500 includes steps 502 through 512. Step 502 provides a source of energy, e.g., microwave energy as supplied by microwave generator 302 of FIG. 4 and/or electrosurgical generator 102 of FIG. 2. Step 504 positions a surgical instrument (e.g., surgical instrument 104 of FIG. 2 or surgical instrument 306 of FIG. 4). Step 506 actives the source of energy. Step 508 estimates the output impedance of the source of energy from step 502. Step 508 may utilize impedance measurement component 128 of FIG. 2 or impedance measurement component 318 of FIG. 4. Step 510 matches the input impedance of the source (from step 502) to about the output impedance. Step 512 adjusts an effective capacitance between the input and output impedances thereby approximately matching the input impedance to the output impedance.

From the foregoing and with reference to the various figure drawings, those skilled in the art will appreciate that certain modification can also be made to the present disclosure without departing from the scope of the same. Therefore, the above description should not be construed as limiting, but merely as exemplifications of particular embodiments. Those skilled in the art will envision other modifications within the scope and spirit of the claims appended hereto.

What is claimed is:

1. A system for performing a surgical procedure, the system comprising:
a source of energy comprising one of an electrosurgical generator or a microwave generator;
a surgical instrument configured to operatively couple to the source of energy and receive energy therefrom, wherein the surgical instrument is adapted to treat tissue with the energy;
a first measurement component and a second measurement component interposed along an energy delivery path;
an impedance matching network interposed on the energy delivery path between the first measurement component and the second measurement component and adapted to match an input impedance of the source of the energy to about an output impedance, wherein the first measurement component is configured to measure at least one input energy property of the energy input into the impedance matching network and the second measurement component is configured to measure at least one output energy property of the energy output by the impedance matching network; and
a power measurement component operatively coupled to the first measurement component and the second measurement component and configured to measure the energy based on the at least one input energy property and the at least one output energy property.

2. The system according to claim 1, wherein the source of the energy includes the impedance matching network.

3. The system according to claim 1, wherein the power measurement component estimates at least one of a total power delivered to tissue, a power reflectance, an instantaneous power delivery to tissue, an energy transfer efficiency and a S-parameter.

4. The system according to claim 1, wherein the impedance matching network continuously matches the input impedance from the source of the energy to the output impedance.

5. The system according to claim 1, wherein the at least one input energy property or the at least one output energy property is selected from the group consisting of a voltage, a current, a duty cycle, a frequency, a power level, an energy efficiency, a reflectance, a wattage, a total power delivered, a power factor, an instantaneous power delivery and a S-parameter.

6. The system according to claim 1, further comprising:
an impedance measurement component adapted to estimate at least one of the input impedance of the source of energy and the output impedance based on the at least one input energy property and the at least one output energy property.

7. The system according to claim 6, wherein the impedance measurement component intermittently estimates the output impedance and operatively communicates the estimated output impedance to the impedance matching network, wherein the impedance matching network intermittently matches the input impedance of the source of the energy to the output impedance in accordance with the communicated and estimated output impedance.

8. The system according to claim 1, further comprising:
a control component operatively coupled to the impedance matching network and adapted to control at least one parameter of the impedance matching network to match the input impedance of the source to the output impedance.

9. The system according to claim 8, wherein the at least one parameter includes at least one of a capacitance, an impedance, an inductance and a resistance.

10. The system according to claim 1, wherein the impedance matching network includes at least one matching element of a balun, a π-network, a T-network, a capacitor, a resistor, a variac, a transformer, an inductor, a variable capacitor, a vacuum variable capacitor, a PIN diode, an RF PIN diode, a FET, a MEMS device, a chip cap, a solid state switch network of chip caps, a stub tuned PC board reactance and a motor driven variable reactive element.

11. The system according to claim 1, wherein the impedance matching network has a capacitance formed from a network having a PIN diode array.

12. An electrosurgical system, the system comprising:
an electrosurgical generator configured to generate electrosurgical energy;
an electrosurgical instrument configured to operatively couple to the electrosurgical generator to receive the electrosurgical energy therefrom, wherein the electrosurgical instrument is adapted to treat tissue with the electrosurgical energy;
a first measurement component and a second measurement component interposed along an energy delivery path;
an impedance matching network interposed on the electrosurgical energy delivery path between the first measurement component and the second measurement component and adapted to match an input impedance of the electrosurgical generator to an output impedance, wherein the first measurement component is configured to measure at least one input energy property of the electrosurgical energy input into the impedance matching network and the second measurement component is configured to measure at least one output energy property of the electrosurgical energy output by the impedance matching network; and
a power measurement component operatively coupled to the first measurement component and the second measurement component and configured to measure the energy based on the at least one input energy property and the at least one output energy property.

13. The system according to claim 12, wherein the electrosurgical generator includes the impedance matching network.

14. The system according to claim 12, wherein the impedance matching network continuously matches the input impedance of the electrosurgical generator to the output impedance.

15. The system according to claim 12, further comprising:
an impedance measurement component adapted to estimate at least one of the input impedance of the electrosurgical generator and the output impedance based on the at least one input energy property and the at least one output energy property.

16. The system according to claim 15, wherein the impedance measurement component intermittently estimates the output impedance and operatively communicates the estimated output impedance to the impedance matching network, wherein the impedance matching network intermittently matches the input impedance of the electrosurgical generator to the output impedance in accordance with the communicated and estimated output impedance.

17. A microwave surgical system for treating tissue, the system comprising:
a microwave generator configured to generate microwave energy;
an antenna configured to operatively couple to the microwave generator to receive the microwave energy therefrom, wherein the antenna is adapted to treat tissue with the microwave energy;
a first measurement component and a second measurement component interposed along a microwave energy delivery path;
an impedance matching network interposed on the microwave energy delivery path between the first measurement component and the second measurement component and adapted to match an input impedance of the microwave generator to an output impedance, wherein the first measurement component is configured to measure at least one input energy property of the microwave energy input into the impedance matching network and the second measurement component is configured to measure at least one output energy property of the microwave energy output by the impedance matching network; and
a power measurement component operatively coupled to the first measurement component and the second measurement component and configured to measure the energy based on the at least one input energy property and the at least one output energy property.

18. A generator for surgical treatment of tissue, the generator comprising:
an energy output stage configured to generate energy being one of electrosurgical energy and microwave energy;
a surgical instrument interface configured to operatively couple to a surgical instrument configured to treat tissue with the energy, wherein the source of the energy operatively communicates the energy to the surgical instrument interface;
a first measurement component and a second measurement component interposed along an energy delivery path;

an impedance matching network interposed on the energy delivery path between the first measurement component and the second measurement component and adapted to match an input impedance of the generator to an output impedance, wherein the first measurement component is configured to measure at least one input energy property of the energy input into the impedance matching network and the second measurement component is configured to measure at least one output energy property of the energy output by the impedance matching network; and a power measurement component operatively coupled to the first measurement component and the second measurement component and configured to measure the energy based on the at least one input energy property and the at least one output energy property.

19. An electrosurgical generator, the generator comprising:

a RF output stage configured to generate electrosurgical energy;

an electrosurgical instrument interface configured to operatively couple to an electrosurgical instrument configured to treat tissue with the electrosurgical energy, wherein the RF output stage operatively communicates the electrosurgical energy to the electrosurgical instrument interface;

a first measurement component and a second measurement component interposed along an energy delivery path;

an impedance matching network interposed on the electrosurgical energy delivery path between the first measurement component and the second measurement component and adapted to match an input impedance of the electrosurgical generator to an output impedance, wherein the first measurement component is configured to measure at least one input energy property of the electrosurgical energy input into the impedance matching network and the second measurement component is configured to measure at least one output energy property of the electrosurgical energy output by the impedance matching network; and a power measurement component operatively coupled to the first measurement component and the second measurement component and configured to measure the energy based on the at least one input energy property and the at least one output energy property.

* * * * *